US008314605B2

(12) United States Patent
Pruckner et al.

(10) Patent No.: US 8,314,605 B2
(45) Date of Patent: Nov. 20, 2012

(54) MEDICAL TREATMENT DEVICE WITH TOOL RECOGNITION

(75) Inventors: Christian Pruckner, Vienna (AT); Andreas Brandstaetter, St. Pantaleon (AT); Wolfgang Wendtner, Lamprechtshausen (AT)

(73) Assignee: W&H Dentalwerk Burmoos GmbH (AT)

( * ) Notice: Subject to any disclaimer, the term of this patent is extended or adjusted under 35 U.S.C. 154(b) by 393 days.

(21) Appl. No.: 12/613,263

(22) Filed: Nov. 5, 2009

(65) Prior Publication Data

US 2010/0109644 A1    May 6, 2010

(30) Foreign Application Priority Data

Nov. 5, 2008   (EP) ..................................... 08019312

(51) Int. Cl.
*G01R 19/22*   (2006.01)
*G01R 31/26*   (2006.01)

(52) U.S. Cl. .................. 324/120; 324/762.01
(58) Field of Classification Search .. 324/762.01–762.1, 324/120, 754.01–754.3; 433/29, 80; 318/568.17
See application file for complete search history.

(56) References Cited

U.S. PATENT DOCUMENTS

| | | | | |
|---|---|---|---|---|
| 3,703,037 | A | * | 11/1972 | Robinson ........................ 433/86 |
| 4,403,956 | A | * | 9/1983 | Nakanishi ....................... 433/29 |
| 6,331,765 | B1 | * | 12/2001 | Yamamoto et al. ........... 323/210 |
| 2007/0234493 | A1 | | 10/2007 | Hilscher et al. |

FOREIGN PATENT DOCUMENTS

| | | |
|---|---|---|
| DE | 3706934 | 9/1988 |
| DE | 3708801 | 9/1988 |
| GB | 2382876 | 6/2003 |
| WO | WO2008/021507 | 2/2008 |

OTHER PUBLICATIONS

European Search Report, EP08019312, 1 page (Apr. 2, 2009).

* cited by examiner

*Primary Examiner* — Tung X Nguyen
(74) *Attorney, Agent, or Firm* — Klarquist Sparkman, LLP

(57) ABSTRACT

A medical treatment device, such as a dental treatment device, is described, the device including a drive unit for driving multiple different tools that are detachably connectable to the treatment device and a tool recognition device for recognizing whether a tool is connected to the treatment device and/or which of the different tools is connected to the treatment device. The tool recognition device includes a coil and an evaluation unit, wherein the coil is connected or connectable to an AC voltage sources, and the coil is inductively couplable to the different tools, so that an AC voltage signal that is specific for each tool and that can be associated with the particular tool by the evaluation unit can be generated.

36 Claims, 3 Drawing Sheets

MEDICAL TREATMENT DEVICE WITH TOOL RECOGNITION

CROSS REFERENCE TO RELATED APPLICATION

The present application claims priority from pending European Patent Application No. 08019312, filed Nov. 5, 2008, which is incorporated herein by reference.

FIELD

The present disclosure relates to a medical treatment device, such as a dental treatment device, having a tool recognition device for recognizing whether a tool is connected to the treatment device and/or which of several different tools is connected to the treatment device. Methods for recognizing whether a tool is connected to the treatment device and/or which of the different tools is connected to the treatment device are also disclosed.

BACKGROUND

One class of prior art treatment device, as disclosed in, e.g., German patent DE 37 08 801 C2, comprises, among other things, a handpiece and a tool recognition device for recognizing different tools connectable to the treatment device. Each tool has a ferrite core and different coils. A measuring coil, which is supplied with an alternating AC voltage from an AC voltage source and is inductively couplable to the different tools, is provided in the treatment device. Based on the input impedance typical of each tool, the AC signal downstream from the coil has a frequency-dependent characteristic, which is likewise typical. A measuring and evaluating device measures the differing electric impedance of the handpiece as a function of the respective tool provided on the handpiece after connecting a tool to the handpiece, taking into account the respective AC voltage frequency, and recognizes the tool on the basis of this impedance measurement.

Conventional tool recognition devices thus have complex designs in terms of the measurement and evaluating technology, in particular to provide multiple measurements at different frequencies and the necessity of providing each tool with a different coil. There thus remains a need to create a treatment device having a tool recognition device with a simpler design in terms of the measurement and evaluation technology.

SUMMARY

Disclosed embodiments of a medical treatment device, such as a dental treatment device, can provide a simpler design for measuring and evaluating a tool connected to the device. One embodiment includes a drive unit for driving multiple different tools detachably connectable to the treatment device and a tool recognition device for recognizing whether a tool is connected to the treatment device and/or which of the different tools is connected to the treatment device. The tool recognition device can comprise a coil and an evaluating unit, wherein the coil is connectable or connected to an AC voltage source and the coil is inductively couplable to the different tools, so that an AC voltage signal that is specific for each tool can be generated. The tool-specific AC voltage signal can be associated with each of the tools. For example, a unique AC voltage can be assignable by the evaluating unit to each individual tool and/or the evaluation unit can store an AC voltage signal associated with each individual tool.

Tool recognition can be accomplished exclusively on the basis of the AC voltage signal, which is modified by the tool (e.g., by electromagnetic induction) such that the design of the measurement and evaluation unit is significantly simplified. The modification, i.e., the increase or decrease in the AC voltage signal, can be caused by the soft-magnetic properties of the tools, which influence the inductance of the coil. Recognition of whether a tool is connected to the treatment device can be based on the same measurement principle, whereby the evaluating unit in this case differentiates only between a first AC voltage signal, which is essentially equal to the AC voltage signal applied at the input end of the coil and is present when no tool is connected to the treatment device, and a second AC voltage signal, which deviates from the AC voltage signal applied at the input end of the coil and is present when a tool is connected to the treatment device.

According to one embodiment, the AC voltage signals that can be assigned to or associated with the respective tools have different amplitudes with different amplitude extreme values, wherein the evaluating unit is designed for differentiating the tools on the basis of at least one amplitude (e.g., an amplitude extreme value). The use of the amplitude extreme values, i.e., the voltage maximums and/or the voltage minimums, guarantees an especially reliable and accurate differentiation of the various tools.

According to one embodiment, the evaluation unit has a converter unit, comprising at least one rectifier and at least one smoothing capacitor, which converts the AC voltage signals that can be assigned to or associated with the respective tools into DC voltage signals. The voltage value of the DC voltage signals can be approximately equal to the voltage value of at least one amplitude extreme value of the respective AC voltage signals.

The AC voltage signals or the DC voltage signals derived therefrom can be evaluated on the basis of at least one amplitude extreme value/voltage extreme value as peak-to-peak detection, in which the evaluating unit ascertains the voltage difference between the maximum voltage values and the minimum voltage values. Alternatively, the evaluation unit can determine the voltage difference between the amplitude extreme values and/or voltage extreme values and a fixed value, in particular the zero point. To do so, either only one or both half-waves of the sinusoidal AC voltage signals are used. If the AC voltage signals are rectified before being evaluated, then this is done by half-wave rectification when using only one half-wave, or full-wave rectification when using both half-waves, resulting in a more stable signal. Regardless of the evaluation method used, each tool has either a specific voltage difference value that can be assigned to or associated with the respective tool or an amount of the voltage difference value that can be assigned to or associated with the respective tool.

In order to obtain a different AC voltage signal which can be assigned unambiguously to or associated with the respective tool and to do so for each tool, in particular for tools which are combined into a tool set and which are possibly being used sequentially or in alternation during a medical treatment, the tools can have different geometries. In particular, the tools can differ in their shaft lengths and/or in their diameters, such as in the diameters of the tool shafts. Alternatively or additionally, the tools can differ in the materials of which they are made or manufactured. The tools can be made of different soft-magnetic materials, e.g., from different steels. However, it is also conceivable that one tool may be made of a non-soft-magnetic material such as, for example, plastic, only to differentiate this at least one tool. Such a tool can be a filling probe for dental filling material, for example.

Because of the different geometries or materials of the tools, it is advantageously not necessary to provide the tools with additional components such as coils or markings for differentiation in some embodiments.

According to one embodiment, a tool set comprises five different tools such as, for example, tools for removing dental calculus (e.g., tartar) or plaque. Each tool has a working segment for acting on a treatment site and a shaft connected thereto for connection or coupling of the tool to the treatment device. The tool shafts have diameters between approximately 3.5 and 5.5 mm, in particular between 4.0 and 5.0 mm, such that each tool shaft has its own specific diameter. To ensure an unambiguous differentiation of tools despite the nonlinear characteristic of the inductance, according to one embodiment, the differential amounts between the diameters of successive tool shafts are different, e.g., the diameters amount to approximately 4.10 mm, 4.20 mm, 4.40 mm, 4.65 mm and 4.90 mm and the differential amounts between the diameters of the successively following tool shafts thus amount to approximately 0.10 mm, 0.20 mm or 0.25 mm.

The tool recognition device can be suitable for differentiating or recognizing different types of tools, e.g., tools intended for a rotating, vibrating, oscillating, and/or reciprocating movement. Accordingly, the drive unit has drives or motors (e.g., electric motors) for driving the tools, which generate a rotating or oscillating movement, the drives being operable by a fluid such as compressed gas, or piezoelectric or magnetostrictive vibration generators. The drive unit can additionally comprise one of more shafts, vibrating axes, gears, couplings, and/or other components, for transmission and/or conversion of the driving movement generated by the drives or motors.

The treatment device can comprise, in addition to the drive unit, a handle element that can be gripped by hand, such as a medical handpiece (e.g., a dental handpiece, contra-angle handpiece, or a pistol-shaped handle piece), a power source or a connection to a power source for supplying power to the treatment device, one or more media sources or connections to one or more media sources (e.g., a water supply or a compressed air source), and supply lines between the handle element and the power source and/or the at least one media source. The tool recognition device can be arranged entirely in the handle element or at least a portion of the tool recognition device, such as at least a portion of the evaluating unit, can be located in the handle element. In some embodiments, the evaluating unit can include a microcontroller or power source arranged outside of the handle element (e.g., in an independent control unit connected to the handle element via a supply tube).

Recognition and differentiation of the different tools can serve to allow resources (e.g., quantities of resources) intended for the tool to be adjusted to the treatment device, in particular to the handle element, to the drive unit, or to the tool. For example, tools that are operated to oscillate have different resonant frequencies, such that the oscillation-inducing drive unit is supplied with different power supply voltages, depending on the tool connected to the treatment device, so that the connected tool can be operated at its resonant frequency as accurately as possible. According to one embodiment, the treatment device is designed as a plaque removing device or a scaler treatment device whose drive unit comprises a vibration generator, such as a piezoelectric generator, which can be supplied with a driving energy, driving power, or driving voltage, and adjusted to the tool as a function of the tool connected to the treatment device and recognized by the tool recognition device.

Alternatively or additionally, in embodiments including different tools that require different coolants or quantities of coolants, the supply unit can deliver a coolant or quantities of coolant (such as, for example, a cooling liquid or a compressed gas) coordinated with the tool.

In order to facilitate delivery of the resources or quantities of resources tailored to the tool by the supply unit, the tool recognition device, in particular the evaluating unit, can be designed to deliver a specific control signal for each tool to the supply unit after recognition of the tool connected to the treatment device. The evaluating unit therefore can include a memory mechanism in which a characteristic value for each tool is stored, such as a characteristic voltage value. The evaluating unit can also include a comparator configured to compare the stored value with the AC voltage signal that is specific for each tool or a signal derived therefrom. Another memory can be provided in the supply unit, storing data about the resources or quantities of resources required for each tool. On the basis of these data, the supply unit can then control the delivery of resources or quantities of resources. The two memories may of course be designed as a shared memory, which is part of the treatment device (e.g., part of the control unit).

According to another embodiment, the treatment device has an illumination device with at least one optical semiconductor element, such as at least one light-emitting diode (LED), wherein a shared electric line such as a dual-core line, is provided for supplying electric power to the illumination device and to the coil of the tool recognition device, such that the coil and the illumination device are electrically connected in parallel. Due to this extremely space-saving design, it is possible to arrange the tool recognition device and the illumination device in immediate proximity to the tool receptacle or the tool coupling of the treatment device. One embodiment of an illumination device comprises multiple LEDs that can be arranged, for example, around the tool coupling.

The shared electric line can be connected or connectable to a power source, which supplies DC voltage for the power supply to the illumination device and supplies AC voltage for the power supply to the coil of the tool recognition device. In order for the shared electric line to be able to supply DC voltage to the illumination device and to supply AC voltage to the coil, the AC voltage can be modulated onto the DC voltage or the two voltages can be superimposed in some embodiments. This can further simplify the arrangement of the coil in the illumination device in the very spatially restricted environment around the tool receptacle or tool coupling because the use of additional electric or electronic components in this area, such as an AC/DC converter, can be omitted in some embodiments.

According to one embodiment, the power source has a DC voltage source, a square-wave or sine-wave oscillator, a capacitor for supplying AC voltage to the coil and a resistor connected in parallel with the capacitor for supplying DC voltage to the at least one optical semiconductor element. The shared electric line can connect this power source to the coil and to the illumination device. It is self-evident, however, that the power source may also have a different design and may have, for example, a DC voltage source and an independent AC voltage source. At least one of the two voltage sources can include a battery.

According to one embodiment, the treatment device comprises a switch element for switching the power supply for the coil and the illumination device between a first operating state, in which the tool recognition is performed, and a second operating state, such that during the first operating state, the DC voltage has a low voltage value and the AC voltage has a high voltage value, and such that during the second operating state, the DC voltage has a high voltage value and the AC voltage has a low voltage value. During the second operating state, the tool can be driven, for example. Switching between these two operating states and/or the different voltage values can help to guarantee optimal tool recognition and optimal operation of the illumination device. In particular, the reduction in the DC voltage protects the light-emitting diode from an excessively high voltage supply during tool recognition, and protects the tool recognition from an influence on or falsification of the measurement signals.

According to one embodiment, the low voltage value of the DC voltage amounts to between approximately 0.9 V per optical semiconductor element and approximately 1.5 V per optical semiconductor element, and can be from approximately 1.1 V per optical semiconductor element to about 1.2 V per optical semiconductor element in some embodiments. The high voltage value of the DC voltage amounts to between approximately 2.5 V per optical semiconductor element and about 3.3 V per optical semiconductor element, and can be from approximately 3.0 V per optical semiconductor element to about 3.2 V per optical semiconductor elements in some embodiments. The low voltage value of the AC voltage can be from approximately 0.0 V to about 0.5 V, and the high voltage value of the AC voltage can be from approximately 10 V to about 18 V (e.g., approximately 15V).

Before the start of tool recognition or after starting operation of the treatment device, the DC voltage for the LEDs can be switched to the low voltage value and then the AC voltage for the coil of the tool recognition device can be switched to the high voltage value. After the conclusion of tool recognition, the AC voltage is first switched to the low voltage value and then the DC voltage is switched to the high voltage value. The switch element can be designed as an electronic circuit, which is part of the microcomputer in the control unit in some embodiments.

A method for recognizing whether a tool is connected to a medical treatment device (e.g., a dental treatment device) as described above or which of the different tools is connected to the treatment device can include a step in which the coil is inductively coupled to one of the different tools, thereby generating an AC voltage signal, which is specific for each tool and can be assigned to or associated with the respective tool by the evaluation unit. The treatment device can include an illumination device with at least one optical semiconductor element, such that according to another method step, the illumination device and the coil of the tool recognition device, which are arranged in parallel, are supplied with electric power via a shared electric line. In particular the power supply for the coil and the illumination device can be switched between a first operating state, in which tool recognition occurs and a second operating state, such that during the first operating state, the DC voltage has a low voltage value and the AC voltage has a high voltage value, and such that the DC voltage during the second operating state has a high voltage value and the AC voltage has a low voltage value.

One disclosed method comprises providing a treatment device, wherein the treatment device comprises a drive unit for driving a plurality of different tools, each tool being detachably connectable to the treatment device, providing a tool recognition device, wherein the tool recognition device comprises a coil and an evaluation unit, wherein the coil is connectable or connected to an AC voltage source, and wherein the coil is inductively couplable to each of the different tools, generating a specific AC voltage signal for each tool, wherein the AC voltage signal can be assigned to or associated with the respective tool by the evaluation unit, and recognizing whether a tool is connected to the medical treatment device and/or recognizing which of the different tools is connected to the treatment device, using the AC voltage signal.

Disclosed methods can also include providing an illumination device with at least one optical semiconductor element in the treatment device and supplying the illumination device and the coil of the tool recognition device with electric power via a shared electric line, wherein the illumination device and the coil are arranged in parallel with one another.

In some methods, a shared electric line configured to supply a variable DC voltage to the illumination device and to supply a variable AC voltage to the coil of the tool recognition device can be provided, wherein the coil and the illumination device are connected in parallel to one another. Some such methods can also include switching the power supply for the coil and the illumination device between a first operating state in which tool recognition is performed and a second operating state, wherein the DC voltage has a low voltage value and the AC voltage has a high voltage value during the first operating state, and wherein the DC voltage has a high voltage value and the AC voltage has a low voltage value during the second operating state.

In another method, a specific control signal for each tool can be delivered to a supply unit, and one or more resources tailored to the tool can be dispensed, the resources comprising at least one of electric driving power, cooling liquid, and compressed gas.

Several embodiments are explained in greater detail below, with reference to the accompanying drawings:

DETAILED DESCRIPTION

Figure 1:
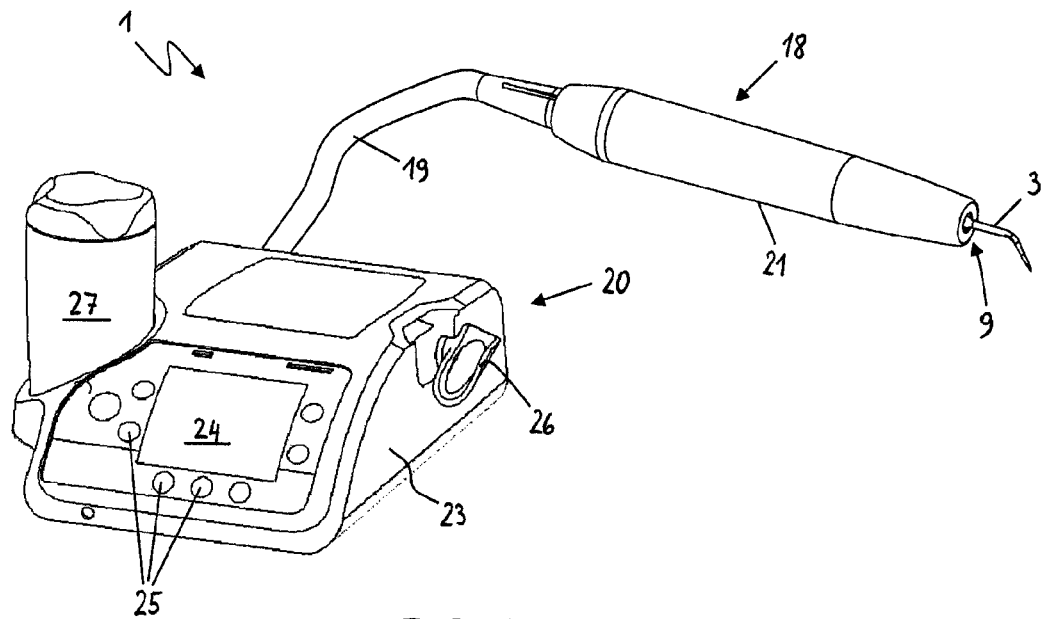
FIG. 1 shows an embodiment of a medical treatment device having a tool recognition device and a handpiece for removal of dental tartar.

The medical treatment device 1 shown in FIG. 1 is embodied as a dental calculus removal device or a scaler treatment device. It comprises a handle element or handpiece 18, a control unit 20 and a supply or connection tubing 19 connecting the control unit 20 and the handpiece 18.

The straight elongated handpiece 18 has a hollow cylindrical outer sleeve 21 in which are arranged the drive unit 2 for a tool 3, 3', 3" connectable to the handpiece 18 (see FIGS. 2, 5A, and 5B), at least parts of the tool recognition device 4 (see FIG. 3), a tool receptacle 22 for detachable accommodation of different tools 3, 3', 3" (see FIG. 2), and an illumination device 9 surrounding the tool receptacle 22. The control unit 20 has a housing 23 with a display 24 for displaying fixed or adjustable operating parameters or the type of tool 3, 3', 3" detected by the tool recognition device 4, one or more adjusting elements 25, such as pushbuttons, for selecting or changing operating parameters, a handpiece rest 26 and a liquid source 27 with a cooling or rinsing liquid.

Figure 3:
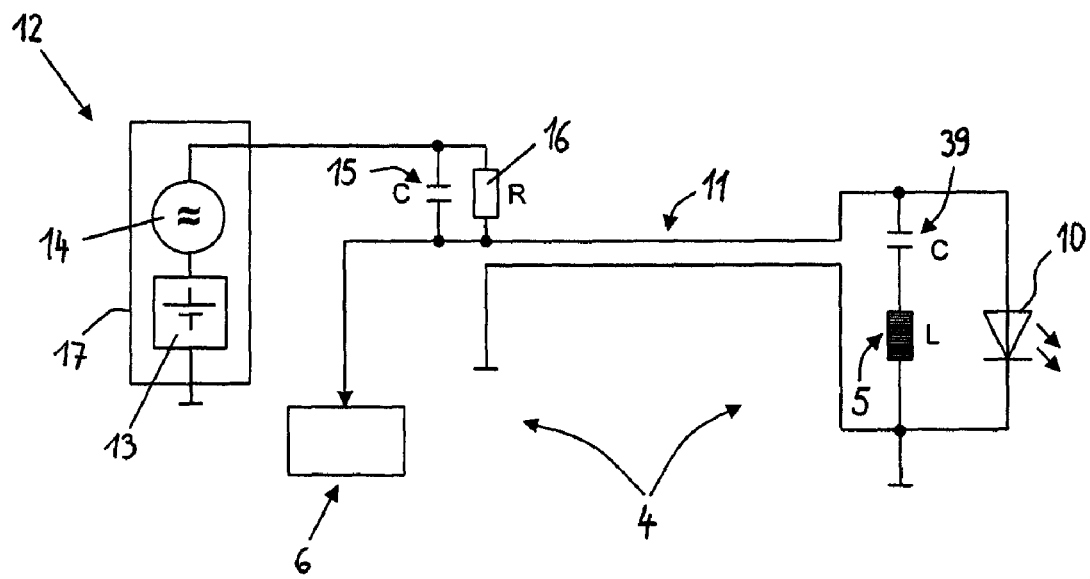
FIG. 3 shows a schematic diagram of an embodiment of a wiring diagram of the tool recognition device.

The power supply or connecting tubing 19 contains multiple media lines or lines for resources, in particular electric lines which connect the drive unit 2 and the tool recognition device 4 to corresponding power sources such as the power source 12, shown in FIG. 3. According to one embodiment, the treatment device has two electric power supply circuits completely separated from one another, wherein one electric power supply circuit supplies electric power to the drive unit 2 and the other electric power supply circuit supplies electric power to the tool recognition device 4. A media line connects the liquid source 27 to the tool receptacle 22 and a tool 3, 3', 3" accommodated therein, so that liquid can be dispensed via a liquid dispensing opening 28 of the tool 3, 3', 3" to the treatment side and/or the tool 3, 3', 3", in particular its working segments 3A, 3'A, 3"A.

Figure 2:
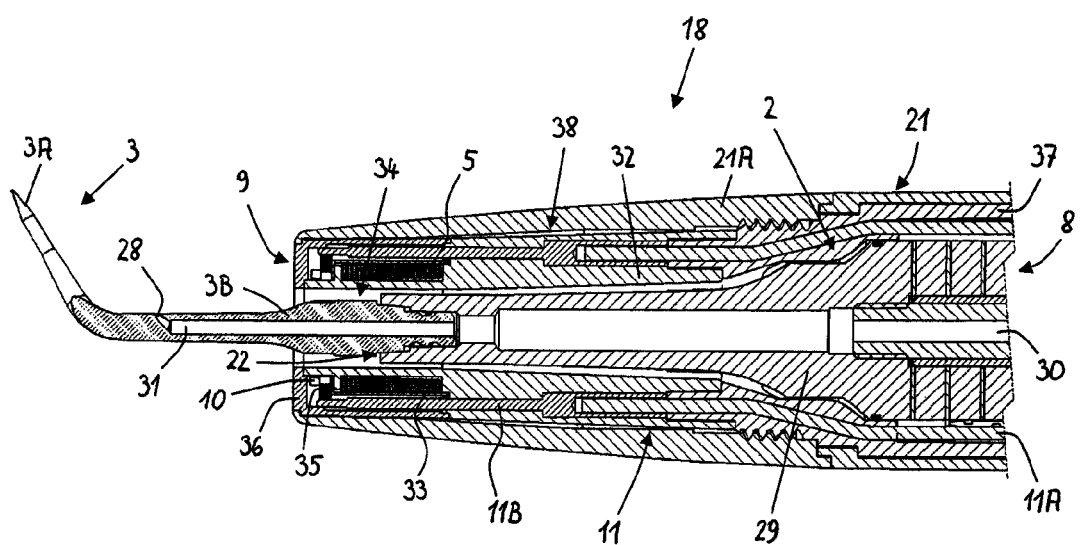
FIG. 2 shows a sectional diagram of the tool end of the handpiece for removal of dental plaque from FIG. 1.

As shown in FIG. 2, the drive unit can comprise a piezoelectric vibration generator 8 having multiple piezoelectric elements and a sonotrode 29 connected to the vibration generator 8 and designed as a hollow oscillating shaft. At one end of the sonotrode 29, the tool receptacle 22 is provided for detachable accommodation of different tools, e.g., tools 3, 3', 3". The tool receptacle 22 comprises, for example, an inside thread, which can be connected to an outside thread of the tool 3, which can be provided on its tool shaft 3B. The tool receptacle 22 may also have a conical friction surface, which forms a frictional engagement with a second conical friction surface of the tool 3, which is provided on its tool shaft 3B in some embodiments. The alternative tools 3', 3" shown in FIGS. 5A and 5B have an inside thread on the tool shaft 3'B, 3"B, which is connectable to a corresponding outside thread of a tool receptacle.

The media line 30 connected to the liquid source 27 opens into the hollow sonotrode 29 from which the cooling liquid is transferred into a channel 31 of the tool 3 to emerge through the liquid dispensing opening 28.

The tool end of the sonotrode 29, the tool receptacle 22 and a tool shaft 3B, 3'B, 3"B accommodated therein are surrounded by the illumination device 9 and a coil 5, which is part of the tool recognition device 4 (see FIG. 3). The cylindrical coil 5 is supported on a carrier sleeve 32 made of plastic. A magnetic return element 33, such as a magnetic return element comprising sheet metal, substantially surrounds the coil on its outside and to a partial extent also on its inside facing the tool shaft 3B, 3'B, 3"B and the sonotrode 29. The sleeve-like return element 33, which is provided with an opening to the inside, produces a bundling or compaction of the magnetic field line or an increase in the magnetic flux density exactly in the geometrically differently shaped areas 34, 34', 34" of the tool shafts 3B, 3'B, 3"B, thereby facilitating a differentiation of tools 3, 3', 3" by the tool recognition device 4.

The illumination device 9, which can include a circuit board 35 and one or more optical semiconductor elements 10 such as, for example, light-emitting diodes, can be arranged distally adjacent to the coil 5. The circuit board 35 can be shaped in the form of ring, so that a tool 3, 3', 3" inserted into the tool receptacle 22 can protrude through its central opening. A transparent plastic sleeve 36 can cover the circuit board 35 and/or the light-emitting diodes 10 and can protects them from soiling and mechanical loads.

The electric power supply to the coil 5 and the illumination device 9 can be accomplished via a shared electric line 11, which comprises an insulated metal wire 11A and metal pins 11B passing through the carrier sleeve 32 and protruding into the transparent sleeve 36. The metal pins 11B have bushings on one end to receive the metal wire 11A or strands of the metal wire 11A. The metal pins 11B contact the circuit board 35 to supply power to the LEDs 10 and contact the ends of the coil 5, so that the coil 5 and the optical semiconductor elements 10 are connected in parallel electrically.

In some embodiments, at least the optical semiconductor elements 10, the circuit board 35 and/or the coil 5 are at least partially cast or encapsulated with a casting material (e.g., an encapsulating material or potting compound), for example, with a synthetic resin (e.g., an epoxy resin), to protect them from external influences and soiling. The optical semiconductor elements 10, the circuit board 35, the coil 5, the return element 33, the transparent sleeve 36, the carrier sleeve 32 and the pins 11B can form a unit 38 that is separable from the remaining handpiece 18 and is attachable to an attachment piece 37 of the handpiece 18, wherein the wire 11A of the electric line 11 also passes through the connecting piece 37. To release or insert this unit 38, the outer sleeve 21 of the handpiece 18 can be divided into two parts and can include a front cap part 21A, which is separable from the remaining outside sleeve 21, e.g., by a screw connection.

Instead of casting, the optical semiconductor elements 10, the circuit board 35, the coil 5, the return element 33, and/or the pins 11B can be hermetically encapsulated. This is accomplished, for example, by welding (e.g., ultrasonic welding) of the transparent sleeve 36 to the carrier sleeve 32.

FIG. 3 shows an embodiment of a tool recognition device 4 including the power source 12 in the form of a schematic wiring diagram. The coil 5 and a light-emitting diode 10 are illustrated on the right side of the diagram. The coil 5 and the light-emitting diode 10 are supplied with electric power via the shared two-stranded electric line 11, wherein the line 11 is divided into two electrically parallel branches, the coil 5 being arranged on one branch and the light-emitting diode 10 being arranged on the other branch. The coil 5 is inductively couplable to the different tools 3, 3', 3" that may be connected to the treatment device 1, so that it is possible to generate an AC voltage signal that is specific for each tool 3, 3', 3" and can be assigned to or associated with a particular tool 3, 3', 3" by the evaluation unit 6. The evaluation unit 6 can compare stored voltage values or values derived from the voltage values (for each tool) to the measured AC voltage values or values derived from the voltage values, respectively.

A capacitor 39 can be connected upstream at the input end of the coil 5, so that the coil 5 and the capacitor 39 together form a resonant circuit or a resonance-generating device for tool recognition. The coil 5 with the series-connected capacitor 39 can be connected in parallel to the diode 10. If a protective circuit, which protects the coil 5 when the light-emitting diode 10 is supplied with DC voltage, is needed for the coil 5, then a protective element, e.g., a resistor or a diode, can be connected upstream from the coil 5.

The power source 12 can comprise a DC voltage source 13, a sine-wave oscillator 14, a capacitor 15 for supplying an AC voltage to the coil 5, and a resistor 16 connected in parallel with the capacitor 15 for supplying a DC voltage to the at least one optical semiconductor 10. The power source thus can be formed by a DC voltage source 12 and an AC voltage source 17, which are connected to the shared electric line 11. At least during tool recognition, a mixed voltage consisting of a superimposed DC voltage and AC voltage can be conducted over the shared electric line 11.

The evaluation unit 6 for analog and digital signal analysis, which includes a controller or a microprocessor in some embodiments, can be connected to the coil 5 and can detect the changes in the AC voltage signals, which are supplied by the AC voltage source 17, said changes being due to the inductive coupling of the coil 5 to the different tools 3, 3', 3". For evaluation of the AC voltage signals and for tool recognition, the evaluation unit 6 can be connected to the input end of the coil 5 or to the output end.

The tool shaft, or the part of the tool shaft couplable (e.g., insertable) into the coil 5 of the tool recognition device 4, can serve as a core that affects the inductance of the coil 5. The AC current in the coil 5 induces a magnetic field. This magnetic field causes a magnetization of the tool shaft, which can comprise a ferrite core. Thus, the magnetic field (or magnetic flux) and the tool shaft affect the inductance of the coil 5 and also the AC voltage received by the evaluation unit 6. Because the material, shape, and/or diameter of each tool shaft can be different from one another, each tool can produce a different magnetic field (magnetic flux), which thus results in different induced AC voltages (e.g., a unique AC voltage for each different tool).

In some embodiments, no initialization of the evaluation unit 6 is required. In some embodiments, initialization prior to measuring the AC voltage with the tool 3 coupled to the tool recognition device 4 (e.g. the tool shaft inserted into the coil 5) can be performed. For example, the AC voltage can be measured without a tool being coupled to the tool recognition device 4, in order to obtain a reference AC voltage value. When a tool is coupled to the tool recognition device 4 and the measurement of the AC voltage is repeated, the recognition of the tool can be based on the reference AC voltage and the measured AC voltage.

Figure 4:
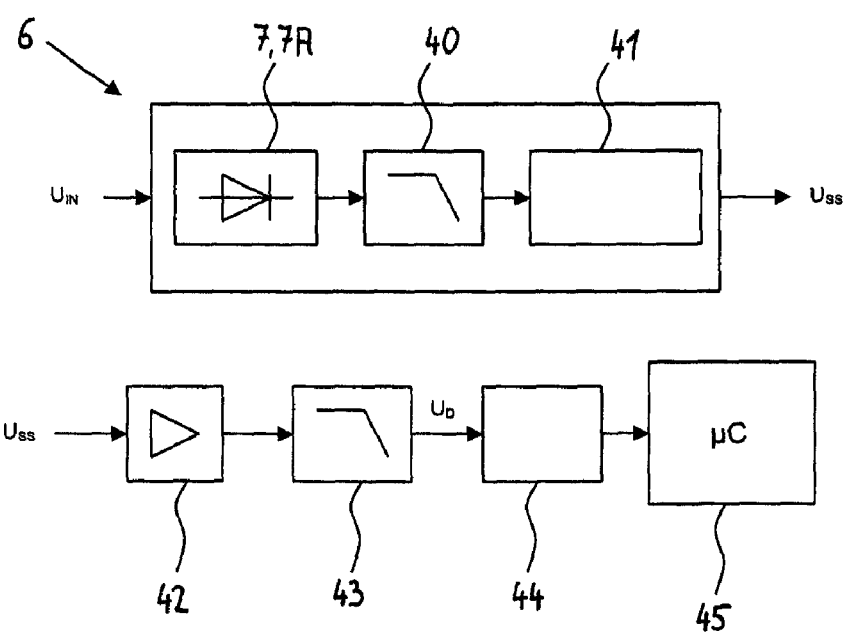
FIG. 4 shows a schematic block diagram of an embodiment of an evaluation unit of the treatment device for evaluating the AC voltage signals.

FIG. 4 shows a schematic block diagram of the design of the evaluation unit 6. The AC voltage signal $U_{IN}$, which is modified by the inductive coupling between the coil 5 and the tool 3, 3', 3", can be sent first to a converter unit 7 comprising a rectifier 7A and a smoothing capacitor, a low-pass filter 40 and a peak-to-peak voltmeter 41. The AC voltage signal $U_{IN}$ is thus converted to a DC voltage signal having two voltage values, such that the voltage values are approximately equal to the voltage values of the amplitude extreme values of the AC voltage signal, i.e., the maximum and minimum voltage peaks of the AC voltage signal. The peak-to-peak voltmeter 41 determines the difference between these two voltage values, which is specific for each tool 3, 3', 3", and generates on the basis of this difference a peak-to-peak measurement signal $U_{SS}$, which is also specific for each tool 3, 3', 3".

The measurement signal $U_{SS}$ is sent to a measurement amplifier 42 and to another low-pass filter 43, is then subjected to a level adjustment 44 and is further processed by an evaluation circuit 45, which can include the microprocessor, so that resources coordinated with the tool 3, 3', 3", e.g., electric driving power, cooling liquid, compressed gas, or quantities of resources tailored to the tool 3, 3', 3", e.g., driving voltages or cooling liquid volume flows, may be dispensed onto the tool 3, 3', 3" through a supply unit connected to the evaluation circuit 45.

Figure 5A:
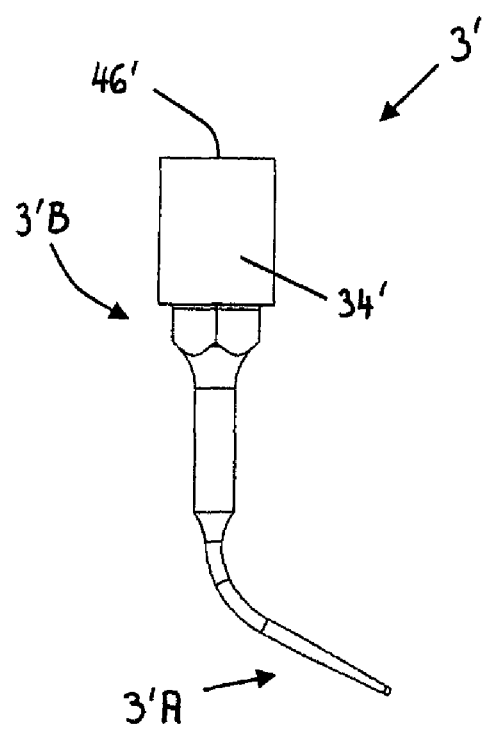
FIGS. 5A and 5B show two different tools which have different shaft diameters for differentiation by a tool recognition device and which can be connected to a medical treatment device, such as a dental treatment device.
Figure 5B:
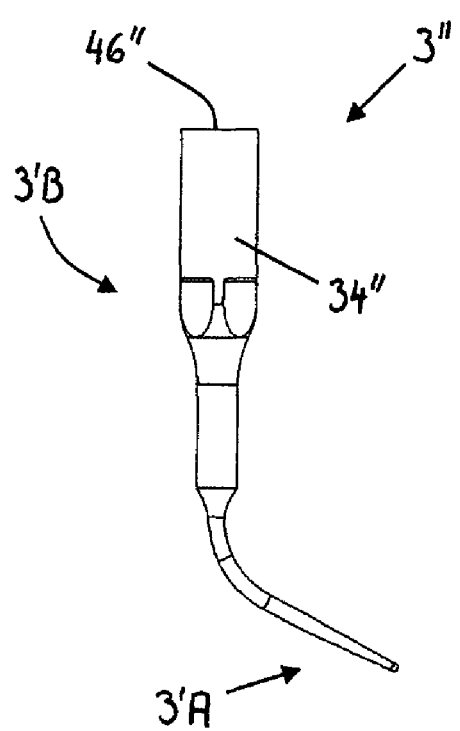

The tools or dental calculus removing tips 3', 3" illustrated in FIGS. 5A and 5B have a working segment 3'A, 3"A and a tool shaft 3'B, 3"B. A hollow cylindrical section 46', 46" having an inside thread for connection to a tool receptacle or coupling is provided on the tool shaft 3'B, 3"B. The hollow cylindrical section 46', 46" also serves as an area 34', 34" of a different geometric shape for differentiation of the tools 3', 3" by the tool recognition device 4. The areas 34', 34" therefore can have different diameters because the wall thicknesses of the hollow cylindrical sections 46', 46" are different, whereas the inside bores of the hollow cylindrical sections 46', 46" with the inside threads have the same diameter. Alternatively or additionally, the areas 34', 34" are of different lengths.

In embodiments where the tools 3', 3" have differently shaped cylindrical portions 46', 46", the air gap between the outer surface of the tools and the coil varies due to the different shapes (e.g., diameters). This results in different magnetic reluctance, thereby affecting the inductance of the coil. Therefore, the AC voltage in the coil varies and results in different induced AC voltages depending on the different tools.

The present invention is not limited to the embodiments described here but instead includes all embodiments which apply or contain the basic appropriate function principle of the invention. Furthermore, the features of the embodiments described and illustrated herein can be combined with one another.

What is claimed is:

1. A medical treatment device, comprising:
a drive unit configured to drive one of a plurality of different tools at a time, each of the different tools being detachably connectable to the treatment device; and
a tool recognition device configured to recognize which of the different tools is connected to the treatment device, wherein the tool recognition device comprises a coil and an evaluation unit, wherein the coil is connectable to an AC voltage source and wherein the coil is inductively couplable to each of the different tools, so that a specific AC voltage signal is generated for each of the different tools, wherein each of the specific AC voltage signals is associated with the respective tool by the evaluation unit, and
wherein the drive unit comprises a vibration generator that can be supplied with a driving energy that is tailored to each of the different tools as a function of the tool that is connected to the treatment device and is recognized by the tool recognition device.

2. The treatment device according to claim 1, wherein each of the AC voltage signals has a different amplitude, and the evaluation unit is configured to differentiate amongst the different tools on the basis of at least the amplitude.

3. The treatment device according to claim 1, wherein the evaluation unit comprises a converter unit that includes at least one rectifier and one smoothing capacitor for converting the AC voltage signals into DC voltage signals.

4. The treatment device according to claim 1, wherein the treatment device comprises a set of different tools, each tool having at least one of a tool shaft of a different geometry and a tool shaft comprised of a different material.

5. The treatment device according to claim 1, wherein the treatment device comprises an illumination device having at least one optical semiconductor element, wherein a shared electric line is configured to supply electric power to the illumination device and to the coil of the tool recognition device, and wherein the coil and the illumination device are connected in parallel to one another.

6. The treatment device according to claim 5, wherein the shared electric line is connectable to a power source to create a power supply that supplies a variable DC voltage to the illumination device and a variable AC voltage to the coil.

7. The treatment device according to claim 6, further comprising a switch element configured to switch the power supply for the coil and the illumination device between a first operating state in which the tool recognition is performed and a second operating state, wherein the DC voltage has a low voltage value and the AC voltage has a high voltage value during the first operating state, and wherein the DC voltage has a high voltage value and the AC voltage has a low voltage value during the second operating state.

8. The treatment device according to claim 1, wherein the evaluation unit comprises a memory in which a characteristic value is stored for each of the different tools, and a comparator configured to compare a selected stored characteristic value with at least one of a detected AC voltage signal for a selected tool and a signal derived from the AC voltage signal for the selected tool to recognize the tool connected to the treatment device from among the plurality of different tools.

9. The treatment device according to claim 8, wherein the characteristic value is a characteristic voltage value.

10. The treatment device according to claim 8, wherein the evaluation unit is configured to deliver a specific control signal for each tool to a supply unit, so that one or more resources tailored to the tool can be dispensed by the supply unit, the resources comprising at least one of electric driving power, cooling liquid, and compressed gas.

11. The treatment device according to claim 1, wherein the tool recognition device is configured such that the inductance of the coil is affected when one of said different tools is coupled to the coil.

12. A medical treatment device, comprising:
a drive unit configured to drive one of a plurality of different tools at a time, each of the different tools being detachably connectable to the treatment device; and
a tool recognition device configured to recognize which of the different tools is connected to the treatment device, wherein the tool recognition device comprises a coil and an evaluation unit, wherein the coil is connectable to an AC voltage source and wherein the coil is inductively couplable to each of the different tools, so that a specific AC voltage signal is generated for each of the different tools, wherein each of the specific AC voltage signals is associated with the respective tool by the evaluation unit, wherein
the treatment device comprises an illumination device having at least one optical semiconductor element, wherein a shared electric line is configured to supply electric power to the illumination device and to the coil of the tool recognition device, and wherein the coil and the illumination device are connected in parallel to one another.

13. The treatment device according to claim 12, wherein the drive unit comprises a vibration generator that can be supplied with a driving energy that is tailored to each of the different tools as a function of the tool that is connected to the treatment device and is recognized by the tool recognition device.

14. The treatment device according to claim 12, wherein the shared electric line is connectable to a power source to create a power supply that supplies a variable DC voltage to the illumination device and a variable AC voltage to the coil.

15. The treatment device according to claim 14, wherein the power source comprises a DC voltage source, a sine-wave oscillator, a capacitor for supplying AC voltage power to the coil, and a resistor that is connected in parallel to the capacitor for supplying DC voltage power to the at least one optical semiconductor element.

16. The treatment device according to claim 14, further comprising a switch element configured to switch the power supply for the coil and the illumination device between a first operating state in which the tool recognition is performed and a second operating state, wherein the DC voltage has a low voltage value and the AC voltage has a high voltage value during the first operating state, and wherein the DC voltage has a high voltage value and the AC voltage has a low voltage value during the second operating state.

17. The treatment device according to claim 16, wherein the low voltage value of the DC voltage is from approximately 0.9 V per optical semiconductor element to approximately 1.5 V per optical semiconductor element; the high voltage value of the DC voltage is from approximately 2.5 V per optical semiconductor element to approximately 3.3 V per optical semiconductor element; the low voltage value of the AC voltage is from approximately 0.0 V to approximately 0.5 V; and the high voltage value of the AC voltage is from approximately 10 V to approximately 18 V.

18. The treatment device according to claim 16, wherein the low voltage value of the DC voltage is from approximately 1.1 V per optical semiconductor element to approximately 1.2 V per optical semiconductor element; the high voltage value of the DC voltage is from approximately 3.0 V per optical semiconductor element to approximately 3.2 V per optical semiconductor element; the low voltage value of the AC voltage is from approximately 0.0 V to approximately 0.5 V; and the high voltage value of the AC voltage is approximately 15 V.

19. The treatment device according to claim 12, wherein each of the AC voltage signals has a different amplitude, and the evaluation unit is configured to differentiate amongst the different tools on the basis of at least the amplitude.

20. The treatment device according to claim 12, wherein the evaluation unit comprises a converter unit that includes at least one rectifier and one smoothing capacitor for converting the AC voltage signals into DC voltage signals.

21. The treatment device according to claim 12, wherein the treatment device comprises a set of different tools, each tool having at least one of a tool shaft of a different geometry and a tool shaft comprised of a different material.

22. The treatment device according to claim 12, wherein the evaluation unit comprises a memory in which a characteristic value is stored for each of the different tools, and a comparator configured to compare a selected stored characteristic value with at least one of a detected AC voltage signal for a selected tool and a signal derived from the AC voltage signal for the selected tool to recognize the tool connected to the treatment device from among the plurality of different tools.

23. The treatment device according to claim 22, wherein the characteristic value is a characteristic voltage value.

24. The treatment device according to claim 22, wherein the evaluation unit is configured to deliver a specific control signal for each tool to a supply unit, so that one or more resources tailored to the tool can be dispensed by the supply unit, the resources comprising at least one of electric driving power, cooling liquid, and compressed gas.

25. The treatment device according to claim 12, wherein the tool recognition device is configured such that the inductance of the coil is affected when one of said different tools is coupled to the coil.

26. A medical treatment device, comprising:
a drive unit configured to drive one of a plurality of different tools at a time, each of the different tools being detachably connectable to the treatment device; and
a tool recognition device configured to recognize which of the different tools is connected to the treatment device, wherein the tool recognition device comprises a coil and an evaluation unit, wherein the coil is connectable to an AC voltage source and wherein the coil is inductively couplable to each of the different tools, so that a specific AC voltage signal is generated for each of the different tools, wherein each of the specific AC voltage signals is associated with the respective tool by the evaluation unit, wherein the evaluation unit comprises a memory in which a characteristic value is stored for each of the different tools, and a comparator configured to compare a selected stored characteristic value with at least one of a detected AC voltage signal for a selected tool and a signal derived from the AC voltage signal for the selected tool to recognize the tool connected to the treatment device from among the plurality of different tools.

27. The treatment device according to claim 26, wherein the characteristic value is a characteristic voltage value.

28. The treatment device according to claim 26, wherein the evaluation unit is configured to deliver a specific control signal for each tool to a supply unit, so that one or more resources tailored to the tool can be dispensed by the supply unit, the resources comprising at least one of electric driving power, cooling liquid, and compressed gas.

29. The treatment device according to claim 26, wherein each of the AC voltage signals has a different amplitude, and the evaluation unit is configured to differentiate amongst the different tools on the basis of at least the amplitude.

30. The treatment device according to claim 26, wherein the evaluation unit comprises a converter unit that includes at least one rectifier and one smoothing capacitor for converting the AC voltage signals into DC voltage signals.

31. The treatment device according to claim 26, wherein the treatment device comprises a set of different tools, each tool having at least one of a tool shaft of a different geometry and a tool shaft comprised of a different material.

32. The treatment device according to claim 26, wherein the drive unit comprises a vibration generator that can be supplied with a driving energy that is tailored to each of the different tools as a function of the tool that is connected to the treatment device and is recognized by the tool recognition device.

33. The treatment device according to claim 26, wherein the treatment device comprises an illumination device having at least one optical semiconductor element, wherein a shared electric line is configured to supply electric power to the illumination device and to the coil of the tool recognition device, and wherein the coil and the illumination device are connected in parallel to one another.

34. The treatment device according to claim 33, wherein the shared electric line is connectable to a power source to create a power supply that supplies a variable DC voltage to the illumination device and a variable AC voltage to the coil.

35. The treatment device according to claim 34, further comprising a switch element configured to switch the power supply for the coil and the illumination device between a first operating state in which the tool recognition is performed and a second operating state, wherein the DC voltage has a low voltage value and the AC voltage has a high voltage value during the first operating state, and wherein the DC voltage has a high voltage value and the AC voltage has a low voltage value during the second operating state.

36. The treatment device according to claim 26, wherein the tool recognition device is configured such that the inductance of the coil is affected when one of said different tools is coupled to the coil.

* * * * *